US011939325B2

(12) United States Patent
Makriyannis et al.

(10) Patent No.: US 11,939,325 B2
(45) Date of Patent: Mar. 26, 2024

(54) PROCESS FOR MAKING BIOLOGICALLY ACTIVE COMPOUNDS AND INTERMEDIATES THEREOF

(71) Applicant: MAKScientific, LLC, Burlington, MA (US)

(72) Inventors: Alexandros Makriyannis, Watertown, MA (US); Kiran Vemuri, Boston, MA (US)

(73) Assignee: MAKScientific, LLC, Burlington, MA (US)

( * ) Notice: Subject to any disclaimer, the term of this patent is extended or adjusted under 35 U.S.C. 154(b) by 27 days.

(21) Appl. No.: 17/443,336

(22) Filed: Jul. 26, 2021

(65) Prior Publication Data

US 2022/0024910 A1    Jan. 27, 2022

Related U.S. Application Data

(60) Provisional application No. 63/056,896, filed on Jul. 27, 2020.

(51) Int. Cl.
*C07D 417/12* (2006.01)
*C07B 59/00* (2006.01)
*C07D 401/12* (2006.01)

(52) U.S. Cl.
CPC .......... *C07D 417/12* (2013.01); *C07B 59/002* (2013.01); *C07D 401/12* (2013.01); *C07B 2200/05* (2013.01)

(58) Field of Classification Search
CPC .. C07D 417/12; C07D 401/12; C07B 59/002; C07B 2200/05
USPC ...................................................... 544/58.2
See application file for complete search history.

(56) References Cited

U.S. PATENT DOCUMENTS

| | | | |
|---|---|---|---|
| 4,256,727 A | 3/1981 | Triplett et al. |
| 4,732,900 A | 3/1988 | Weber et al. |
| 5,155,124 A | 10/1992 | Kimata et al. |
| 5,208,231 A | 5/1993 | Kimata et al. |
| 5,462,960 A | 10/1995 | Barth et al. |
| 5,624,941 A | 4/1997 | Barth et al. |
| 5,925,768 A | 7/1999 | Barth et al. |
| 6,028,084 A | 2/2000 | Barth et al. |
| 6,344,474 B1 | 2/2002 | Maruani et al. |
| 6,432,984 B1 | 8/2002 | Barth et al. |
| 6,509,367 B1 | 1/2003 | Martin et al. |
| 7,119,108 B1 | 10/2006 | Makriyannis et al. |
| 7,393,842 B2 | 7/2008 | Makriyannis et al. |
| 7,521,471 B2 | 4/2009 | Barth et al. |
| 7,745,440 B2 | 6/2010 | Makriyannis et al. |
| 7,872,006 B2 | 1/2011 | Moritani et al. |
| 8,084,451 B2 | 12/2011 | Makriyannis et al. |
| 8,410,097 B2 | 4/2013 | Makriyannis et al. |
| 8,853,205 B2 | 10/2014 | Makriyannis et al. |
| 10,053,444 B2 | 8/2018 | Makriyannis et al. |
| 2004/0248956 A1 | 12/2004 | Hagmann et al. |
| 2005/0054679 A1 | 3/2005 | Kruse et al. |
| 2007/0117858 A1 | 5/2007 | Xia et al. |
| 2008/0146614 A1 | 6/2008 | Cheng |

FOREIGN PATENT DOCUMENTS

| | | |
|---|---|---|
| EP | 0656354 B1 | 6/1997 |
| WO | 0069848 A1 | 11/2000 |
| WO | 03027076 A2 | 4/2003 |
| WO | 03040107 A1 | 5/2003 |
| WO | 03063781 A2 | 8/2003 |
| WO | 2004060367 A1 | 7/2004 |
| WO | 2004094407 A1 | 11/2004 |
| WO | 2005000820 A2 | 1/2005 |
| WO | 2010104488 A1 | 9/2010 |

OTHER PUBLICATIONS

Bioorganic & Medicinal Chemistry Letters (2019), 29(21), 126644 pp. 1-8.*
Bergman, Jack et al., "Some effects of CB1 antagonists with inverse agonist and neutral biochemical properties," Physiol Behav. 93, 666-670 (2008).
Chambers, Adam P. et al., "A neutral CB1 receptor antagonist reduces weight gain in rat," Am J Physiol Regul Integr Comp Physiol. 293, R2185-2193 (2007).
Cluny, Nina L. et al., "The neutral cannabinoid CB receptor antagonist AM4113 regulates body weight through changes in energy intake in the rat," Pharmacol Biochem Behav. 97, 537-543 (2011).
Cluny, NL et al., "A novel peripherally restricted cannabinoid receptor antagonist, AM6545, reduces food intake and body weight, but does not cause malaise, in rodents," Br J Pharmacol. 161, 629-642 (2010).
Crocker, Peter J. et al., "The role of fluorine substitution in the structure-activity relationships (SAR) of classical cannabinoids," Bioorganic & Medicinal Letters 17, 1504-1507 (2007).
Fan, Hong et al., "Analogs of JHU75528, a PET ligand for imaging of cerebral cannabinoid receptors (CB1): Development of ligands with optimized lipophilicity and binding affinity," European J of Med Chem 44, 593-608 (2009).

(Continued)

*Primary Examiner* — Kahsay Habte
(74) *Attorney, Agent, or Firm* — Alix, Yale & Ristas, LLP

(57) ABSTRACT

A process of manufacturing biologically active compounds, their analogs, pharmaceutically acceptable salts, solvates, polymorphs, isotopic variants, and intermediates thereof. Notably, the compounds of the formula IA, 1B, 1C. 1D. 1E, 1F and IG for which novel processes have been disclosed, selectively act on the cannabinoid receptors, and with high affinity. The processes for the preparation of the compounds enable the syntheses of cannabinoid modulators on a large-scale that are eco-friendly and economically viable. Additionally, the processes disclosed enable the synthesis of cannabinoid modulators with high purity and in high yield for their use in making drug substance and drug products.

12 Claims, 1 Drawing Sheet

(56) References Cited

OTHER PUBLICATIONS

Hodge, Janel et al., "The cannabinoid CB1 receptor inverse agonist AM 251 and antagonist AM 4113 produce similar effects on the behavioral satiety sequence in rats," Behav Brain Res. 193, 298-305 (2008).
Holla, B. Shivarama et al., "Studies in biheterocycles. Part VI. A novel transformation during acid-catalyzed Indolization of ethyl alpha-(arylhydrazono)furan-2-propionates," Indian J Chem 21B(7), 638-641, CAPLUS, doc. No. 97:216073 (1982).
Howlett, Allyn C. et al., "Azido- and Isothiocyanato-Substituted Aryl Pyrazoles Bind Covalently to the CB1 Cannabinoid Receptor and Impair Signal Transduction," J Neurochem, vol. 74, No. 5, 2176-2180 (2000).
Jarbe, Torbjorn U. C. et al., "Central mediation and differential blockade by cannabinergics of the discriminative stimulus effects of the cannabinoid CB(1) receptor antagonist rimonabant in rats," Psychopharmacology, Mar. 3, 2011.
Jarbe, T.U.C. et al., "Intrinsic effects of AM4113, a putative neutral CB1 receptor selective antagonist, on open-field behaviors in rats," Pharmacol Biochem Behav. 91, 84-90 (2008).
Kubinyi, H. "3D QSAR in Drug Design. Theory Methods and Applications. Ligand—Protein Interactions and Molecular Similarity," vol. 2-3, Springer, p. 243-244, (1998).
Lange, Jos H. M. et al., "Bioisosteric Replacements of the Pyrazole Moiety of Rimonabant: Synthesis, Biological Properties, and Molecular Modeling Investigations of Thiazoles, Triazoles, and Imidazoles as Potent and Selective CB1 Cannabinoid Receptor Antagonists," J Med Chem 48, 1823-1838 (2005).
Lange, Jo H. M. et al., "Synthesis, SAR and intramolecular hydrogen bonding pattern of 1,3,5-trisubstituted 4,5-dihydropyrazoles as potent cannabinoid CB1 receptor antagonists," Bioorganic and Medicinal Chemistry Letters 20, p. 1752-1757 (2010).
Limebeer, CL et al., "Inverse agonism of cannabinoid CB1 receptors potentiates LiCl-induced nausea in the conditioned gaping model in rats," Br J Pharmacol. 161, 336-349 (2010).
Patani George A. et al., "Bioisosterism: A Rational Approach in Drug Design," Chem. Rev. 96, 3147-3176 (1996).
Ranatunge Ramani R. et al., "Synthesis and Selective Cyclooxygenase-2 Inhibitory Activity of a Series of Novel, Nitric Oxide Donor-Containing Pyrazoles," J. Med. Chem. 47, 2180-2193 (2004).
Randall, P. A. et al., "The novel cannabinoid CB1 antagonist AM6545 suppresses food intake and food-reinforced behavior," Pharmacol Biochem Behav. 97, 179-184 (2010).
Sink, K.S. et al., "Oral bioavailability of the novel cannabinoid CB1 antagonist AM6527: effects on food-reinforced behavior and comparisons with AM4113," Pharmacol Biochem Behav. 91, 303-306 (2009).
Sink, K.S. et al. "The CB1 inverse agonist AM251, but not the CB1 antagonist AM4113, enhances retention of contextual fear conditioning in rats," Pharmacol Biochem Behav. 95, 479-484 (2010).
Sink, K.S. et al., "Potential anxiogenic effects of cannabinoid CB1 receptor antagonists/inverse agonists in rats: comparisons between AM4113, AM251, and the benzodiazepine inverse agonist FG-7142," European Neuropsychopharmacol. 20, 112-122 (2010).
Sink, Kelly S. et al., "The novel cannabinoid CB1 receptor neutral antagonist AM4113 suppresses food intake and food-reinforced behavior but does not induce signs of nausea in rats, " Neuropsychopharmacology. 33, 946-955 (2008).
Storr, M. A. et al., "Differential effects of CB(1) neutral antagonists and inverse agonists on gastrointestinal motility in mice," Neurogastroenterol Motil. 22, 787-796, e223 (2010).
Tam, Joseph et al., "Peripheral CB1 cannabinoid receptor blockade improves cardiometabolic risk in mouse models of obesity," J Clin Invest. 120, 2953-2966 (2010).
Terfloth, Lothar et al., "Electronic Screening: Lead Finding from Database Mining," in The Practice of Medicinal Chemistry, Ch. 9, Wermuth, 2nd Ed. (2003).
Polinsky, Alex "High-Speed Chemistry Libraries: Assessment of Drug-Likeness," in The Practice of Medicinal Chemistry, Ch. 10, Wermuth, 2nd Ed. (2003).

\* cited by examiner

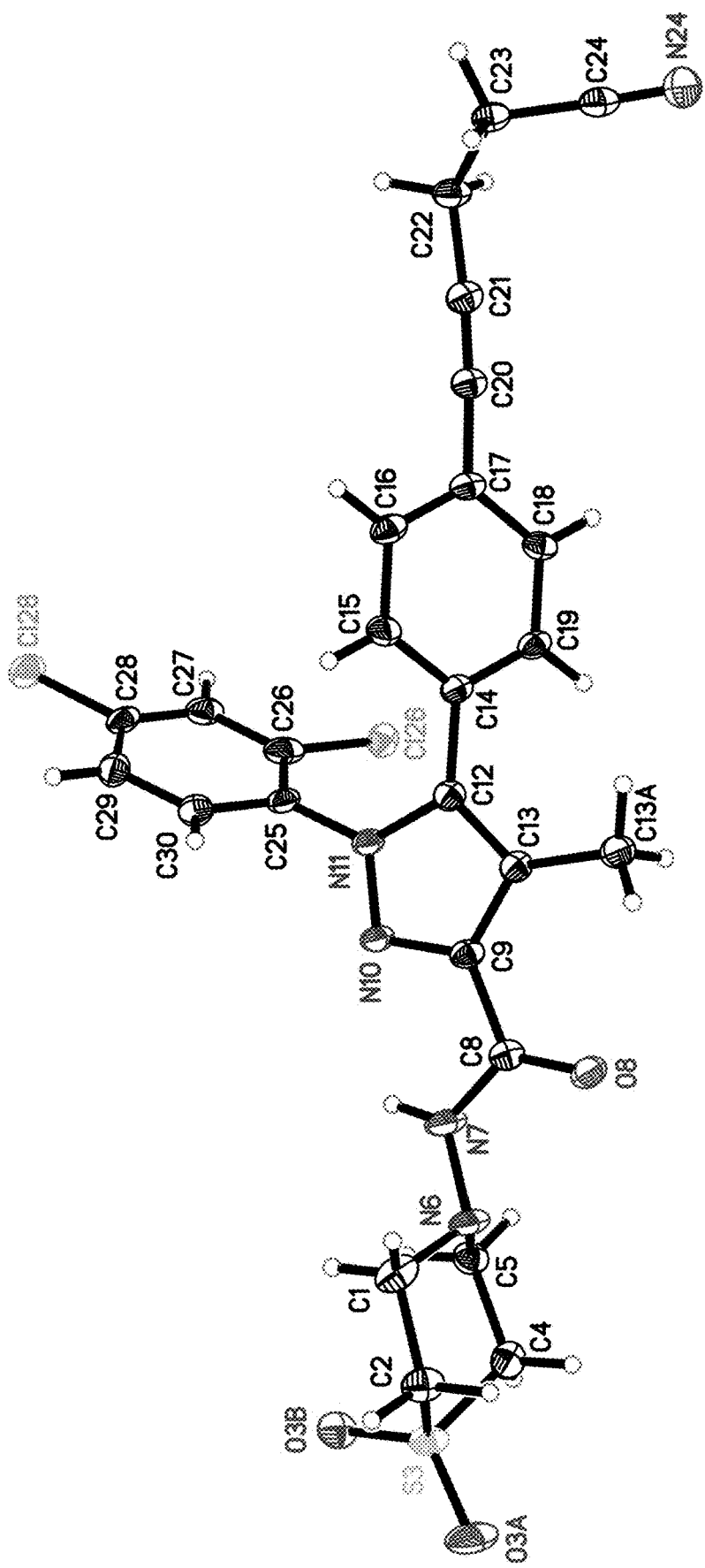

PROCESS FOR MAKING BIOLOGICALLY ACTIVE COMPOUNDS AND INTERMEDIATES THEREOF

BACKGROUND

The present invention relates to a chemical process for the preparation of compounds of one of Formulae I, IA, IB, IC, ID, IE, IF and IG, and IV, IVA, IVB, IVC, V and VI and intermediates thereof.

More specifically, the invention relates to a chemical process for the preparation of 5-[4-(4-cyano-1-butyn-1-yl) phenyl]-1-(2,4-dichlorophenyl)-N-(1,1-dioxido-4-thiomorpholinyl)-4-methyl-1H-pyrazole-3-carboxamide and 5-(4-(4-cyanobut-1-yn-1-yl)phenyl)-1-(2,4-dichlorophenyl)-4-methyl-N-morpholino-1H-pyrazole-3-carboxamide and their analogs, solvates, polymorphs and isotopic variations thereof.

Compounds of this class with unique pharmacological properties and therapeutic value have been disclosed in WO200674445, WO2008154015 and WO2010104488.

SUMMARY

Disclosed herein are processes for the preparation of compounds comprising, reacting a compound of Formula II with a compound of Formula III to provide a compound of Formula VII, second by reacting a compound of Formula VII with an alkyne in the presence of a palladium reagent and copper (I) iodide, in a basic medium and in an aprotic solvent to obtain a product of Formula I, third by hydrolysis of a compound of the Formula I using an alkali metal hydroxide to provide a compound of Formula V, and fourth by reacting a compound of Formula V with a substituted hydrazine.

Disclosed herein are processes for the preparation of compounds comprising, reacting a compound of Formula II with a compound of Formula III to provide a compound of Formula VII, second by reacting a compound of Formula VII with an alkyne in the presence of a palladium reagent and copper (I) iodide, in a basic medium and in an aprotic solvent to obtain a product of Formula I, third by reacting a compound of Formula I with a substituted hydrazine, and fourth by reacting a compound of Formula VI with a divinyl derivative.

Disclosed herein are processes for the preparation of compounds comprising, reacting a compound of Formula II with a compound of Formula III to provide a compound of Formula I, second by hydrolysis of a compound of the Formula I using an alkali metal hydroxide to provide a compound of Formula V, and third by reacting a compound of Formula V with a substituted hydrazine.

Specifically, the disclosed herein are alternative processes for preparing compounds comprising, first reacting a compound of Formula II with a compound of Formula III to obtain product of the Formula VII, second by reacting a compound of Formula VII with an alkyne in the presence of a palladium reagent such as tetrakis(triphenylphosphine)palladium(0) and copper (I) iodide, in a basic medium and in an aprotic solvent to obtain a product of Formula I, and third by reacting the product of the Formula I using an alkali metal hydroxide to provide a compound of Formula V, fourth by reacting a compound of Formula V with 4-aminothiomorpholine 1,1-dioxide.

Specifically, the disclosed herein are alternative processes for preparing compounds comprising, first reacting a compound of Formula II with a compound of Formula III to obtain product of the Formula VII, second by reacting a compound of Formula VII with an alkyne in the presence of a palladium reagent such as tetrakis(triphenylphosphine) palladium(0) and copper (I) iodide, in a basic medium and in an aprotic solvent to obtain a product of Formula I, and third by reacting the product of the Formula I using an alkali metal hydroxide to provide a compound of Formula V, fourth by reacting a compound of Formula V with a substituted hydrazine hydrate to obtain a product of the Formula VI, and fifth by reacting a compound of Formula VI with divinyl sulfone.

Disclosed herein are also processes for preparing compounds comprising, first reacting a compound of Formula III with a substituted hydrazide to obtain product of the Formula IV, second by reacting a compound of Formula IV with Formula II Disclosed herein are also processes for preparing compounds comprising, first reacting a compound of Formula III with a substituted hydrazide to obtain product of the Formula IV, second by reacting a compound of Formula IV with Formula II to obtain a compound of Formula ID, third by reacting compound of the Formula 1D with an alkyne in the presence of a palladium reagent such as tetrakis(triphenylphosphine)palladium(0) and copper (I) iodide, in a basic medium and in an aprotic solvent.

Certain embodiments disclose processes for the preparation of compounds of one of Formulae I, IA, IB, IC, ID, IE, IF and IG, and IV, IVA, IVB, IVC, V and VI and intermediates thereof.

BRIEF DESCRIPTION OF THE DRAWINGS

FIG. 1 shows single-crystal X-ray diffraction data of 5-(4-(4-cyanobut-1-yn-1-yl)phenyl)-1-(2,4-dichlorophenyl)-N-(1,1 dioxidothiomorpholino)-4-methyl-1H-pyrazole-3-carboxamide collected using Cu Kα radiation and a Bruker Bruker Photon 100 CMOS area detector.

DETAILED DESCRIPTION

The disclosed embodiments concern a novel process for making each of biologically active compounds of one of Formulae I, IA, IB, IC, ID, IE, IF and IG, and IV, IVA, IVB, IVC, V and VI and intermediates thereof.

More specifically. the disclosed invention concerns a novel process for making each of biologically active compounds of one of Formulae IA, IC and intermediates thereof.

Particularly, in a certain embodiment, a subject of the present invention is a process for preparing a compound of Formula I:

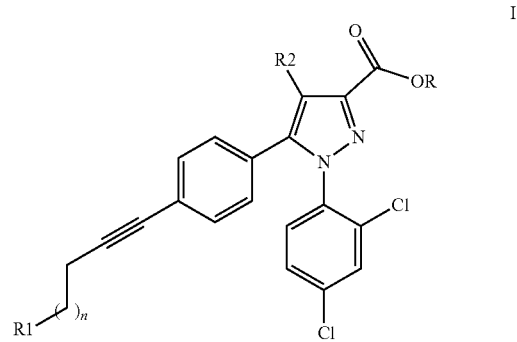

in which:
- R1 is H, CN, OH, phthalimido, mesylate, tosylate, amide, nitrate ester, carboxylic ester, methoxy, halogen
- R2 is H, CH3 or CH2CH3, OCH3 or CN
- R is selected from the group consisting of H, CH3 or CH2CH3
- n is 1-4 comprising steps of reacting a phenylboronic acid derivative of Formula II:

$$\text{II}$$

in which X2 is:
- halogen or where R1 is as defined as in Formula I
with a compound of Formula III $$\text{III}$$

in which:
- R is as defined as in Formula I
- Y is selected from the group consisting of a (C$_1$-C$_4$)alkyl group, a (C$_1$-C$_4$)perfluoroalkyl group, a phenyl group that is unsubstituted or substituted with a methyl, chloro and nitro group in a solvent, in the presence of a catalyst in a basic medium, at a suitable temperature.

In another embodiment, a subject of the present invention is a process for preparing a compound of Formula 1A:

$$\text{IA}$$

in which:
- R1 is H, CN, OH, phthalimido, amide, carboxylic ester, nitrate ester, halogen, methoxy, mesylate or tosylate;
- R2 is CH3, CH2CH3, OCH3 or CN
- n is 1-4
- X1 is CH2, O or SO2 comprising reacting a phenylboronic acid derivative of Formula II with a compound of Formula IV $$\text{IV}$$

in which:
- R2, Y and X1 are defined as in Formula IA and Formula III in a solvent, in the presence of a catalyst in a basic medium, at a suitable temperature.

In another embodiment, a subject of the present invention is a process for preparing a compound of Formula 1B

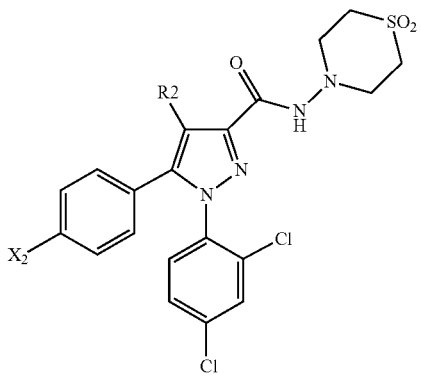

in which:
R2 is CH3, CH2CH3, OCH3 or CN
X2 is defined as in Formula II
Comprising reacting a phenylboronic acid derivative of Formula II with a compound of Formula IVA

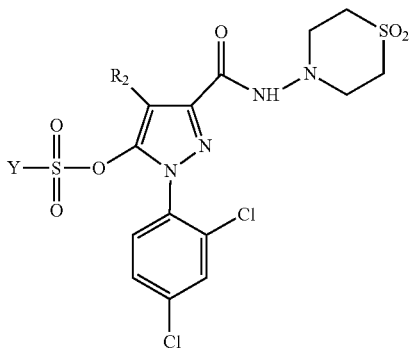

in which:
Y is as defined as in Formula III and Formula IV
R2 is defined as in Formula I and Formula IA
in a solvent, in the presence of a catalyst in a basic medium, at a suitable temperature.

Preferably, the reaction of a compound of Formula II with a compound of Formula III, Formula IV or Formula IVA is carried out in an aromatic solvent, for example toluene, xylene or in an ethereal solvent, for example tetrahydrofuran, dimethoxyethane or in dioxane, or in ethyl acetate, in the presence of a palladium reagent such as tetrakis(triphenylphosphine)palladium(0), and in a basic medium, for example in the presence of an alkali metal carbonate such as sodium carbonate or potassium carbonate. The reaction can be carried out at temperatures ranging from ambient room to 100 deg C.

According to a preferred embodiment, the reaction is carried out in a two-phase medium, in the presence of tetrakis(triphenylphosphine)palladium(0), the basic medium consisting of sodium carbonate or potassium carbonate as an aqueous solution.

In a preferred process for preparing a compound of Formula I, a phenylboronic acid derivative of Formula II is reacted with a compound of Formula III in which Y represents a group $CF_3$, namely a compound of Formula IIIA

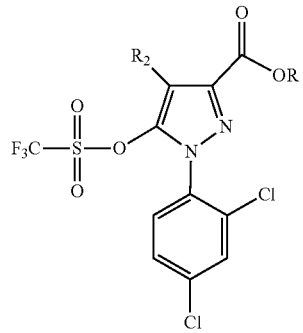

R2 is defined as in Formula I and Formula IA
R is as defined as in Formula I

In addition, according to a preferred process for preparing a compound of Formula IA, a phenylboronic acid derivative of Formula II is reacted with a compound of Formula IV in which Y represents a group $CF_3$, namely a compound of Formula IVB

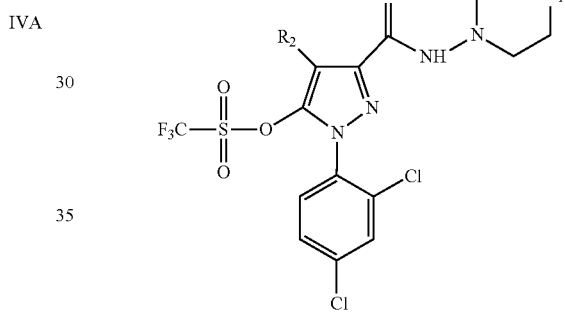

X1 is CH2, O or SO2
R2 is defined as in Formula I and Formula IA

In addition, in a preferred process for preparing a compound of Formula IB, a phenylboronic acid derivative of Formula II is reacted with a compound of Formula IVA in which Y represents a group $CF_3$, namely a compound of Formula IVC

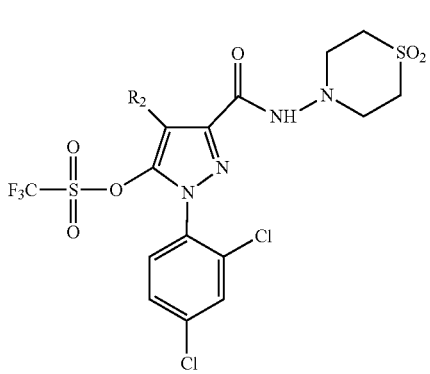

R2 is defined as in Formula I and Formula IA
Preferably, (4-(4-(1,3-dioxoisoindolin-2-yl)but-1-yn-1-yl)phenyl)boronic acid, (4-(4-hydroxybut-1-yn-1-yl)phenyl)

boronic acid, (4-(4-cyanobut-1-yn-1-5 yl)phenyl)boronic acid, (4-(4-((methylsulfonyl)oxy)but-1-yn-1-yl)phenyl)boronic acid, (4-(4-(tosyloxy)but-1-yn-1-yl)phenyl)boronic acid or (4-(5-amino-5-oxopent-1-yn-1-yl)phenyl)boronic acid are reacted with a compound of Formula III or IIIA.

Preferably, (4-(4-(1,3-dioxoisoindolin-2-yl)but-1-yn-1-yl)phenyl)boronic acid, (4-(4-hydroxybut-1-yn-1-yl)phenyl)boronic acid, (4-(4-cyanobut-1-yn-1-yl)phenyl)boronic acid, (4-(4-((methylsulfonyl)oxy)but-1-yn-1-yl)phenyl)boronic acid, (4-(4-(tosyloxy)but-1-yn-1-yl)phenyl)boronic acid or (4-(5-amino-5-oxopent-1-yn-1-yl)phenyl)boronic acid is also reacted with a compound of Formulae IVA or IVC.

More preferably, 4-chlorophenylboronic acid or 4-bromophenylboronic acid is reacted with a compound of Formula IVA or Formula IVC.

In a preferred embodiment, the compound of Formula IV, Formula IVA, Formula IVB and Formula IVC are synthesized from Formula III.

In particular, compound of Formula IV, Formula IVA, Formula IV and Formula IVC are synthesized from Formula IIIA.

To prepare a compound of Formula IV, Formula IVA, Formula IVB and Formula IVC, a compound of Formula III or Formula IIIA is reacted with an appropriate substituted hydrazine, the reaction being carried out in the presence of a Lewis acid.

In particular, to prepare a compound of Formula IV, Formula IVA, Formula IVB and Formula IVC, a compound of Formula III or Formula IIIA is reacted with an appropriate substituted hydrazine, the reaction being carried out in the presence of aluminum chloride.

In particular, to prepare a compound of Formula IV, Formula IVA, Formula IVB and Formula IVC, a compound of Formula III or Formula IIIA is reacted with a substituted hydrazine, the reaction being carried out in the presence of aluminum chloride at temperatures ranging from −15 deg C. to 100 deg C.

In particular, to prepare a compound of Formula IV, Formula IVA, Formula IVB and Formula IVC, a compound of Formula III or Formula IIIA is reacted with a substituted hydrazine, the reaction being carried out in the presence of aluminum chloride at temperatures ranging from −15 deg C. to 100 deg C. in a solvent selected from dichloroethane, toluene, dioxane or tetrahydrofuran.

As a preferred embodiment, the substituted hydrazine can be hydrazine monohydrate, 1-aminopiperidine, 4-aminomorpholine, 4-aminothiomorpholine 1,1-dioxide or 4-aminothiomorpholine 1,1-dioxide-2,2,3,3,5,5,6,6-d8.

In another embodiment, disclosed herein is a process for preparing a compound of Formula IA characterized in that the hydrolysis of a compound of the Formula I using an alkali metal hydroxide such as lithium hydroxide, sodium hydroxide or potassium hydroxide will provide a compound Formula V

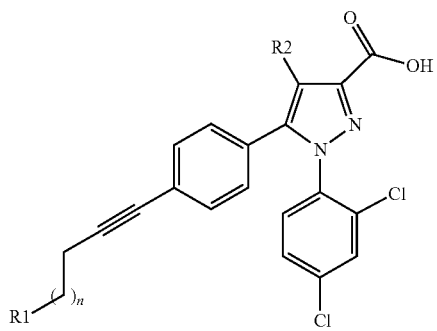

in which:
R1 and R2 as defined as in Formula I and Formula IA
n is 1-4

The subsequent steps involving, the sodium salt of a compound of Formula V being dissolved in water and then washed with a water immiscible solvent such as ethyl acetate, a chlorinated solvent such as dichloromethane or an aromatic solvent such as toluene, or an ethereal solvent such as diethyl ether. The washed water layer containing the sodium salt of a compound of Formula V is then acidified with a mineral acid such as hydrochloric acid in water to obtain a compound of Formula V in highly purified form as free acid.

The subsequent step involving stirring the compound of Formula V in an alcohol such as methanol, ethanol or 2-propanol in the presence of a catalytic amount of mineral acid such as sulfuric acid to provide a highly purified ester of a compound of Formula I.

In the following step, as a preferred embodiment, a compound of Formula I is reacted with hydrazine monohydrate in an ethereal solvent such as tetrahydrofuran, dioxane, or a polar aprotic solvent such as dimethylformamide, dimethylacetamide, or an alcohol such as methanol, ethanol or 2-propanol to provide a compound of Formula VI

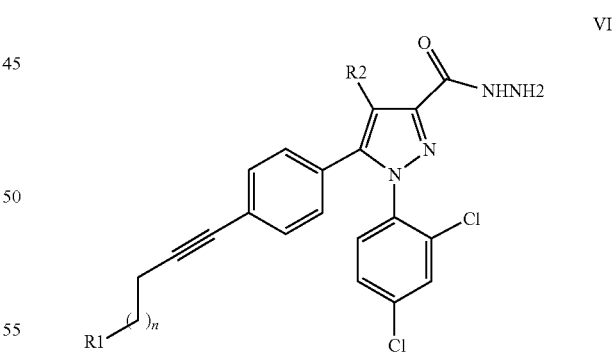

R1 and R2 as defined as in Formula I and Formula IA
n is 1-4

In a preferred embodiment, a compound of Formula IA is prepared by reacting a compound of Formula V with hydrazine monohydrate in ethanol at temperatures ranging from ambient room to 100 deg C. to provide a compound of Formula VI.

Finally, in a certain embodiment, a compound of Formula VI is reacted with divinyl sulfone in the presence of an organic base, preferably a tertiary amine, in an alcohol such as methanol, ethanol or 2-propanol, at temperatures ranging from −15 deg C. to 100 deg C. to provide a compound of Formula VII.

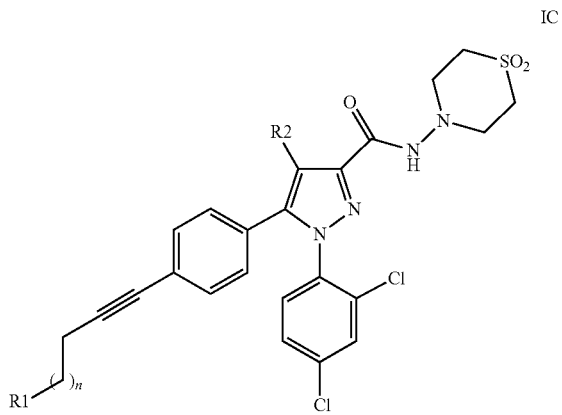

R1 and R2 as defined as in Formula I and Formula IA
n is 1-4

In a preferred embodiment, a compound of Formula VI is reacted with divinyl sulfone in an alcohol such as methanol, ethanol, or 2-propanol at temperatures ranging from −15 deg C. to 100 deg C. to provide a compound of Formula IC in highly purified form.

In another embodiment, to prepare a compound of the Formula IA, IB, IC, ID, IE, IF, and IG, a compound of the Formula V or Formula VIII is reacted with a substituted hydrazine such as 1-aminopiperidine, 4-aminomorpholine, 4-aminothiomorpholine 1,1-dioxide or 4-aminothiomorpholine 1,1-dioxide-2,2,3,3,5,5,6,6-d8 in the presence of a peptide coupling reagent such as N,N,N',N'-tetramethyl-O-(benzotriazol-1-yl)uronium tetrafluoroborate or (1-cyano-2-ethoxy-2-oxoethylidenaminooxy)dimethylamino-morpholino-carbenium hexafluorophosphate in the presence of an amine such as triethyl amine, diisopropyl amine or diisopropyl ethylamine and in a solvent such as dichloromethane, an ethereal solvent such as tetrahydrofuran, a polar aprotic solvent such as dimethylformamide, or a more environmentally acceptable and sustainable alternative such as dimethyl carbonate, ethyl acetate or methyltetrahydrofuran.

In one embodiment, 4-bromophenylboronic acid is reacted with a compound of Formula IVB to provide a compound of Formula ID.

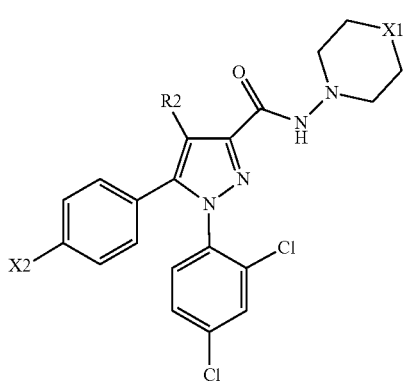

R2 as defined as in Formula I and Formula IA
X1 is CH2, O or SO2
X2 is defined as in Formula II In a subsequent step, the compound of formula ID is reacted with an alkyne in the presence of a palladium reagent such as tetrakis(triphenylphosphine)palladium(0), copper (I) iodide, and in a basic medium, for example in the presence of an amine such as triethyl amine, diisopropyl amine or diisopropyl ethylamine and in an ethereal solvent such as tetrahydrofuran, dioxane or a polar aprotic solvent such as dimethylformamide, or in ethyl acetate to provide a compound of formula 1A. The reaction can be carried out at temperatures ranging from ambient room to 100 deg C.

More preferably, in an embodiment, 4-bromophenylboronic acid is reacted with a compound of Formula III or IIIA to provide a compound of Formula VII

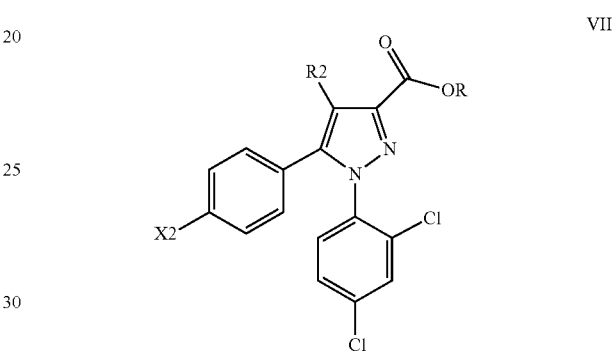

R2 is defined as in Formula I and Formula IA
R is as defined as in Formula I
X2 is defined as in Formula II In a subsequent step, the compound of formula VII is reacted with an alkyne in the presence of a palladium reagent such as tetrakis(triphenylphosphine)palladium(0), copper (I) iodide, and in a basic medium, for example in the presence of an amine such as triethyl amine, diisopropyl amine or diisopropyl ethylamine and in an ethereal solvent such as tetrahydrofuran, dioxane or a polar aprotic solvent such as dimethylformamide, or in ethyl acetate to provide a compound of Formula I. The reaction can be carried out at temperatures ranging from ambient room to 100 deg C.

Following this, in a preferred embodiment, hydrolysis of a compound of the Formula 1 using an alkali metal hydroxide such as lithium hydroxide, sodium hydroxide or potassium hydroxide will provide a compound Formula V.

The steps comprise the sodium salt of a compound of Formula V being dissolved in water and then washed with a water immiscible solvent such as ethyl acetate, a chlorinated solvent such as dichloromethane or an aromatic solvent, for example toluene, or an ethereal solvent such as diethyl ether, tetrahydrofuran, dioxane. The subsequent washed water layer containing the sodium salt of a compound of Formula V is then acidified with a mineral acid such as hydrochloric acid in water to obtain a compound of Formula V in highly purified form as free acid.

The subsequent step comprises stirring the compound of Formula V in an alcohol such as methanol, ethanol or 2-propanol in the presence of a catalytic amount of mineral acid such as sulfuric acid to provide a highly purified ester of a compound of Formula I.

In the following step, a compound of Formula I is preferably reacted with hydrazine monohydrate in an ethereal solvent such as tetrahydrofuran, dioxane, or a polar aprotic solvent such as dimethylformamide, dimethylacetamide, or an alcohol such as ethanol or 2-propanol to provide a compound of Formula VI.

In a preferred embodiment, a compound of Formula IA is prepared by reacting a compound of Formula V with hydrazine monohydrate in ethanol at temperatures ranging from ambient room to 100 deg C. to provide a compound of Formula VI.

Finally, a compound of Formula VI is reacted with divinyl sulfone in the presence of an organic base, preferably a tertiary amine, in an alcohol such as methanol, ethanol or 2-propanol at temperatures ranging from −15 deg C. to 100 deg C. to provide a compound of Formula 1A.

In a preferred embodiment, a compound of Formula VI is reacted with divinyl derivative such as divinyl sulfone in an alcohol such as methanol, ethanol, or 2-propanol at temperatures ranging from −15 deg C. to 100 deg C. to provide a compound of Formula 1A in highly purified form.

In a certain embodiment, hydrolysis of a compound of the Formula VII using an alkali metal hydroxide such lithium hydroxide, sodium hydroxide or potassium hydroxide in a solution containing water mixed with an ethereal solvent such as tetrahydrofuran and an alcohol such as methanol or ethanol will provide a compound Formula VIII.

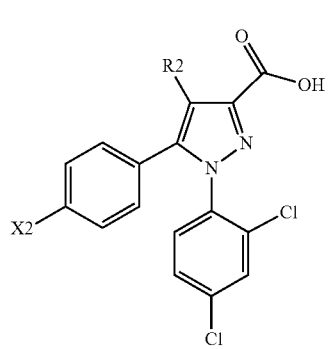

VIII

R2 is defined as in Formula I and Formula IA
X2 is defined as in Formula II

The steps include the sodium salt of a compound of Formula VIII being dissolved in water and then washed with a water immiscible solvent such as ethyl acetate, a chlorinated solvent such as dichloromethane or an aromatic solvent, for example toluene, or an ethereal solvent such as diethyl ether, tetrahydrofuran, dioxane. The subsequent washed water layer containing the sodium salt of a compound of Formula VIII is then acidified with a mineral acid such as hydrochloric acid in water to obtain a compound of Formula VIII in highly purified form as free acid.

The subsequent step comprises stirring the compound of Formula VIII in an alcohol such as methanol, ethanol or 2-propanol in the presence of a catalytic amount of mineral acid such as sulfuric acid to provide a highly purified ester of a compound of Formula VII.

In the following step, a compound of Formula VII is reacted with hydrazine monohydrate in an ethereal solvent such as dimethylformamide, dioxane, or a polar aprotic solvent such as dimethylformamide, dimethylacetamide, or an alcohol such as ethanol or 2-propanol to provide a compound of Formula IX.

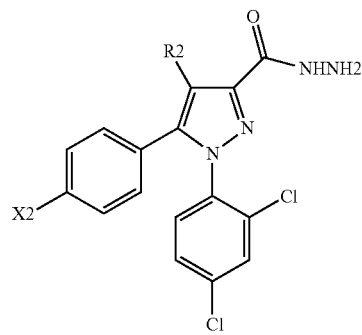

IX

R2 is defined as in Formula I and Formula IA
X2 is defined as in Formula II

In a preferred embodiment, a compound of Formula VII is reacted with hydrazine monohydrate in ethanol at temperatures ranging from ambient room to 100 deg C. to provide a compound of Formula IX.

In a preferred embodiment, a compound of Formula IX is reacted with divinyl sulfone in the presence of an organic base, preferably a tertiary amine, in an alcohol such as methanol, ethanol or 2-propanol at temperatures ranging from −15 deg C. to 100 deg C. to provide a compound of Formula IE.

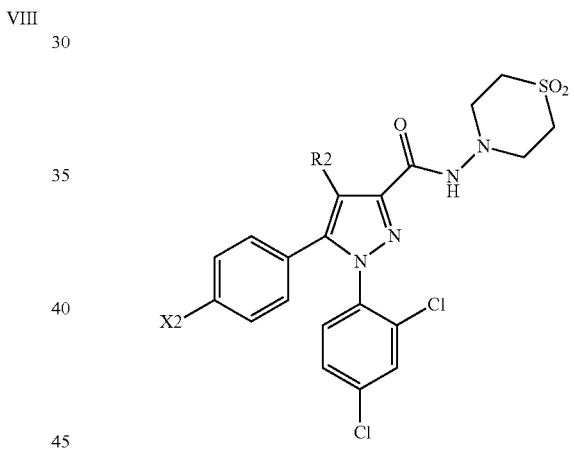

IE

R2 is defined as in Formula I and Formula IA
X2 is defined as in Formula II

In a preferred embodiment, a compound of Formula IX is reacted with divinyl sulfone in an alcohol such as methanol, ethanol, or 2-propanol at temperatures ranging from −15 deg C. to 100 deg C. to provide a compound of Formula IE in highly purified form.

In a subsequent step, the compound of formula IE is reacted with an alkyne in the presence of a palladium reagent such as tetrakis(triphenylphosphine)palladium(0), copper (I) iodide, and in a basic medium, for example in the presence of an amine such as triethyl amine, diisopropyl amine or diisopropyl ethylamine and in an ethereal solvent such as tetrahydrofuran, dioxane or a polar aprotic solvent such as dimethylformamide, or in ethyl acetate to provide compound of Formula IC. The reaction can be carried out at temperatures ranging from ambient room to 100 deg C.

In another embodiment, a compound of Formula VIII is reacted with 4-1,1-dioxide-2,2,3,3,5,5,6,6-d8 in the presence of a peptide coupling reagent such as 2-(1H-benzotriazole-1-yl)-1,1,3,3-tetramethylaminium tetrafluoroborate and an amine such as triethyl amine, diisopropyl amine or diisopropyl ethylamine, and in a chlorinated solvent such as dichloroethane or dichloromethane, or an ethereal solvent such as tetrahydrofuran, methyl tetrahydrofuran, dioxane, or a polar aprotic solvent such as dimethylformamide, or N-methyl pyrrolidinone to provide a compound of the formula IF.

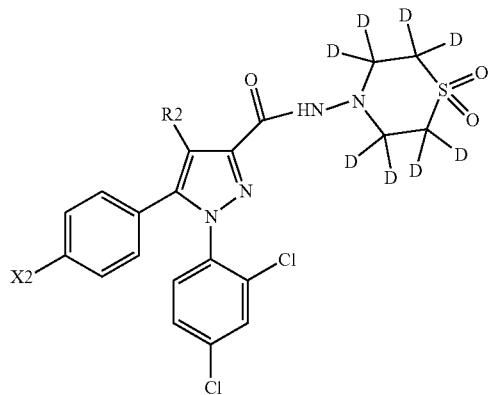

R2 is defined as in Formula I and Formula IA
X2 is defined as in Formula II

Another embodiment includes a reaction wherein the compound of formula IE is reacted with an alkyne in the presence of a palladium reagent such as tetrakis(triphenylphosphine)palladium(0), copper (I) iodide, and in a basic medium, for example in the presence of an amine such as triethyl amine, diisopropyl amine or diisopropyl ethylamine and in an ethereal solvent such as tetrahydrofuran, dioxane or a polar aprotic solvent such as dimethylformamide, or in ethyl acetate to provide compound of Formula IG. The reaction can be carried out at temperatures ranging from ambient room to 100 deg C.

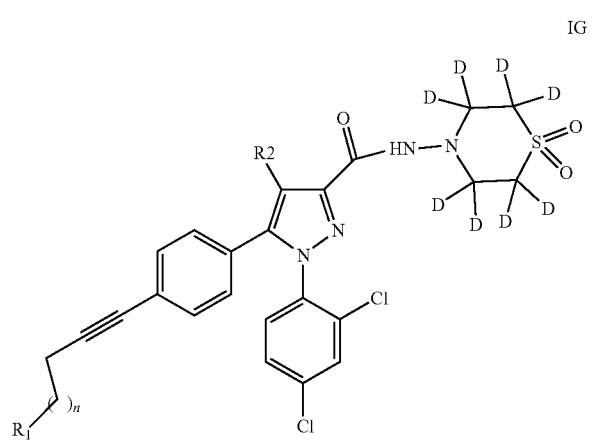

R1 and R2 are defined as in Formula IA and Formula IA
n is 1-4

As a variation, the compounds of the Formulae I, IA, IB, IC, ID, IE, IF, IG and intermediates thereof can also comprise isotopes at one or more of their atoms. For example, the compounds can be radiolabeled with isotopes, such as 2H (deuterium written as D), 3H (tritium written as T), 11C (carbon-11), 13C (carbon-13), 14C (carbon-14), 15O (oxygen-15), 17O (oxygen-17), 18O (oxygen-18), 13N (nitrogen-13), 15N (nitrogen-15), 18F (fluorine-18), 75Br (bromine-75), 76Br (bromine-76), 77Br (bromine-77), 82Br (bromine-82), 123I (iodine-123), 124I (iodine-124), 125I (iodine-125) or 131I (iodine-131), 36Cl (chlorine-36) or 35S (sulphur-35), The present disclosure encompasses all isotopic variations of the described compounds, whether natural or unnatural, radioactive or not.

In some embodiments the amide is defined as any group with the formula —C(O)NH2-, —NH2C(O)—, C(O)NHalkyl-, -alkylNHC(O)—, In some embodiments, the ester group is defined as any group with the formula —C(O)Oalkyl- or —OC(O)-alkyl.

In some embodiments, the compounds have at least one isotope atom incorporated at or adjacent to a site that is susceptible to metabolism. The isotope atom can be part or adjacent to a substituent group as defined.

In some embodiments, the compounds have at least one deuterium atom incorporated at or adjacent to a site that is susceptible to metabolism. The deuterium atom can be part or adjacent to a group as defined.

In certain embodiments, the compounds disclosed herein are synthesized hydrates and also as solvates wherein solvent molecules able to become a partner of crystallization can include water; methanol, ethanol, 2-methoxyethanol, isopropanol, 1-methyl butanol, DMF, NMP, DMSO, methylcyclohexane, dimethylacetamide, 1,4 dioxane and ethyl acetate.

The compounds disclosed herein can exist as various novel and stable polymorphs including hydrated and crystalline forms including solvates.

Several embodiments disclosed herein are described herein. It will be recognized that one or more features of any embodiments disclosed herein may be combined and/or rearranged within the scope of the invention to produce further embodiments that are also within the scope of the invention.

Still other objects and advantages of the disclosed embodiments will become apparent by those of skill in the art from the disclosure herein, which are simply illustrative and not restrictive. Thus, other embodiments will be recognized by the ordinarily skilled artisan without departing from the spirit and scope of the invention.

The disclosure is further illustrated by the following examples, which are not to be construed as limiting this disclosure in scope or spirit to the specific procedures described in this disclosure. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

EXAMPLES

The following examples (Examples 1-3), and schematically shown as Scheme 1, Scheme 2, Scheme 3A, Scheme 3B, and Scheme 4, illustrate specific exemplary steps for performing the above described processes forming the basis of the invention disclosed herein:

Scheme 1
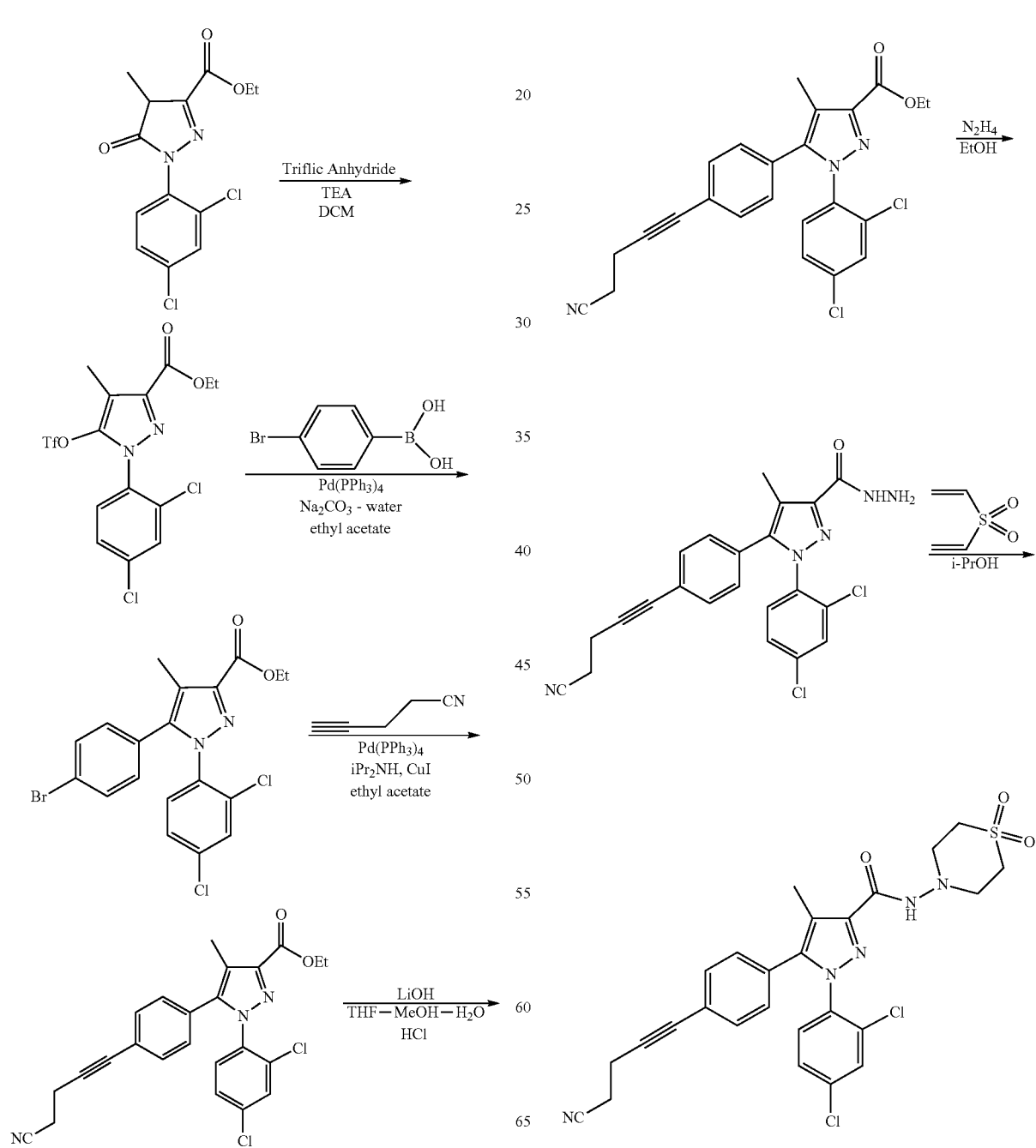

Scheme 2
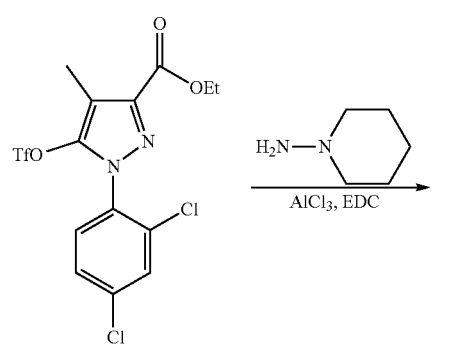
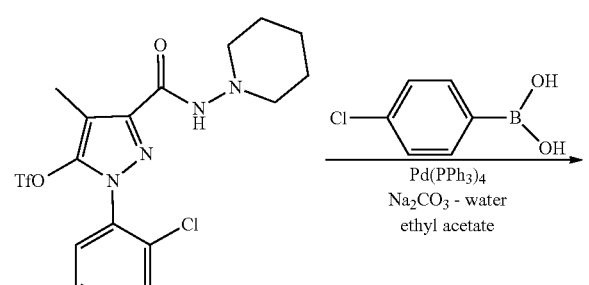
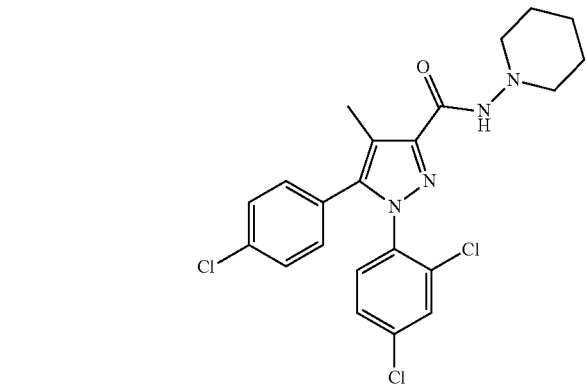
Scheme 3A
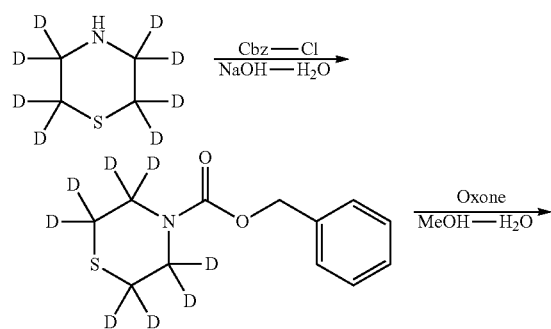
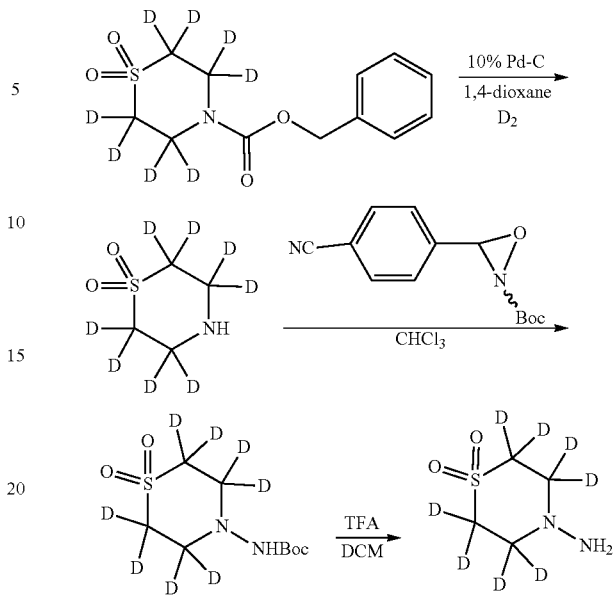
Scheme 3B
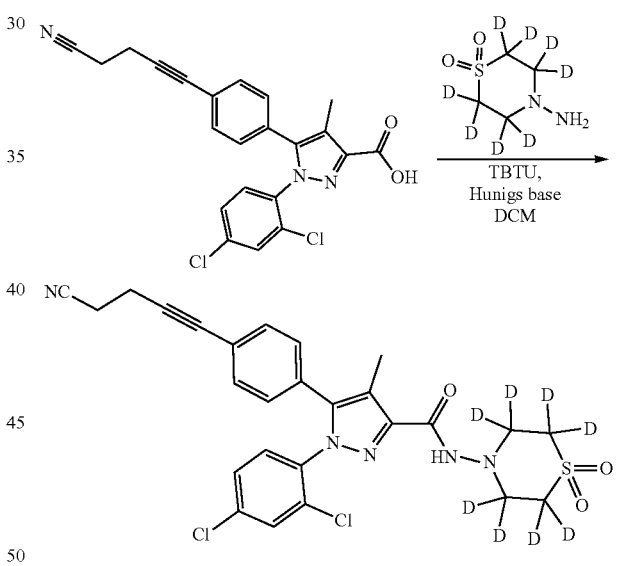
Scheme 4
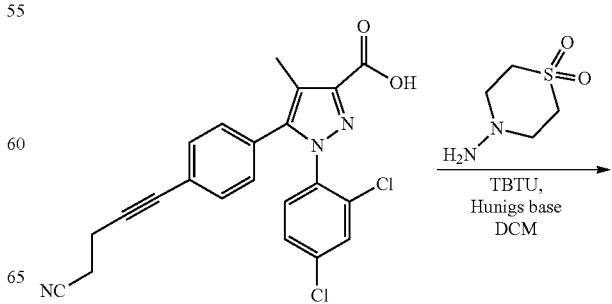

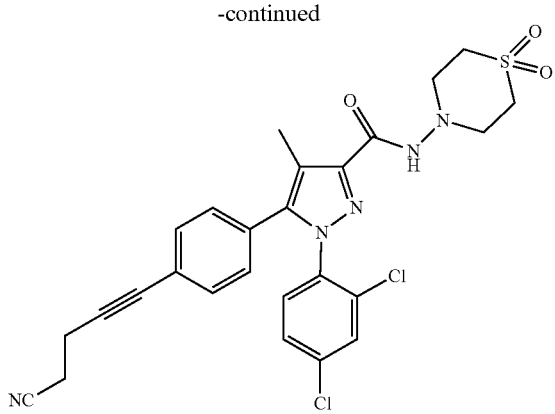

Example 1 (Scheme 1)

A) Ethyl 5-(4-chlorophenyl)-1-(2,4-dichlorophenyl)-4-methyl-1H-pyrazole-3-carboxylate 2,4-Dichlorophenylhydrazine hydrochloride (126 g) is dissolved in 1l of toluene and this solution is placed under nitrogen; after stirring, 100 g of diethyl 2-methyl-3-oxosuccinate are added and the mixture is then heated and 50 ml of TFA are added at 55° C. The mixture is left at the reflux of the solvent for 4 and a half hours, with stirring. The mixture is allowed to return to ambient temperature and is then heated to 75° C. and the reaction medium is hydrolyzed with 300 ml of water. The mixture is separated by settling out, the aqueous phase is discarded, and the organic phase is then evaporated in order to eliminate the residual TFA. The organic phase is taken up with 100 ml of toluene and the expected product then crystallizes (102 g).

B) Ethyl 1-(2,4-dichlorophenyl)-4-methyl-5-(((trifluoromethyl)sulphonyl)oxy)-1H-pyrazole-3-carboxylate Pyrazolone (50 gm) obtained in the preceding step is suspended in 250 ml of DCM, under nitrogen, and the mixture is cooled to 0° C. with stirring. 24 ml of TEA followed by 30 ml of triflic anhydride are added and the stirring is maintained at 0° C. for 15 minutes. The reaction medium is hydrolyzed with 200 ml of DCM. The reaction medium is separated by settling out and the organic phase is then washed with 200 ml of water. The aqueous phase is discarded. The organic phase is evaporated, and the oil obtained is chromatographed on silica, elution being carried out with a pentane/EtOAc mixture (90/10; v/v). The fractions containing the expected compound are combined and evaporated to dryness to obtain the final product (67.7 g).

C) Ethyl 5-(4-bromophenyl)-1-(2,4-dichlorophenyl)-4-methyl-1H-pyrazole-3-carboxylate 25.5 g of the pyrazole triflate of the preceding step, 10.8 g of 4-bromophenylboronic acid and 670 mg of tetrakis (triphenylphosphine)palladium are mixed, under nitrogen; 250 ml of ethyl acetate and 71 ml of a 2M aqueous sodium carbonate solution are added. The reaction medium is stirred at 65° C. for 6 hours. The reaction medium is separated by settling out, the aqueous phase is discarded, and the organic phase is then washed with 100 ml of water. After separation by settling out, the organic phase is evaporated off. The crude product obtained is purified by chromatography on silica, elution being carried out with a cyclohexane/EtOAc mixture (85/15; v/v) to provide the final product (18.9 g).

D) Ethyl 5-(4-(4-cyanobut-1-yn-1-yl)phenyl)-1-(2,4-dichlorophenyl)-4-methyl-1H-pyrazole-3-carboxylate To a stirred solution of bromo compound obtained from the previous step (18 g) in ethyl acetate (400 ml), under argon was added 4-cyano-1-butyne (10 g), and diisopropyl amine (7.8 ml). The reaction mixture was degassed by introducing a steady stream of argon into the solution for 5 min and to this was added tetrakis(triphenylphosphine) palladium (0) (1.8 g) and copper(I) iodide (400 mg). The resulting mixture was refluxed for 3 h. The solvent was washed with deionized water (2×~100 mL). The organic layer was separated, dried over anhydrous MgSO4, filtered and the filtrate was removed in vacuo. The residue obtained was carried to the next reaction without further purification.

E) 5-(4-(4-Cyanobut-1-yn-1-yl)phenyl)-1-(2,4-dichlorophenyl)-4-methyl-1H-pyrazole-3-carboxylic acid The acid (7.5 g, 15.8 mmol) obtained was taken in a 500 ml single neck flask equipped with a nitrogen inlet and to it 200 ml of anhydrous ethyl alcohol. To this was added few drops of sulfuric acid and the mixture was refluxed for 12 hours. The solvents were removed, and the residue was dissolved in dichloromethane (100 ml) and washed with deionized water (2×~100 mL). The organic layer was separated, dried over anhydrous MgSO4, filtered and the solvent was evaporated in vacuo to provide the ester as an off-white solid (7 g, 87%).

F) Ethyl 5-(4-bromophenyl)-1-(2,4-dichlorophenyl)-4-methyl-1H-pyrazole-3-carboxylate The acid (7.5 g, 15.8 mmol) obtained was taken in a 500 ml single neck flask equipped with a nitrogen inlet and to it 200 ml of anhydrous ethyl alcohol. To this was added few drops of sulfuric acid and the mixture was refluxed for 12 hours. The solvents were removed, and the residue was dissolved in dichloromethane (100 ml) and washed with deionized water (2×~100 mL). The organic layer was separated, dried over anhydrous MgSO4, filtered and the solvent was evaporated in vacuo to provide the ester as an off-white solid (7 g, 87%).

G) 5-(4-(4-cyanobut-1-yn-1-yl)phenyl)-1-(2,4-dichlorophenyl)-4-methyl-1H-pyrazole-3-carbohydrazide The ester (7 g, 15.4 mol) obtained was taken in a 500 ml single neck flask equipped with a nitrogen inlet and to it 50 ml of anhydrous ethyl alcohol followed by 20 g of hydrazine hydrate are added and the mixture is heated at reflux for 3 hours. The reaction medium is concentrated in vacuo with 10% residual solvent remaining. The combined residue is dissolved in dichloromethane (150 ml) and washed with deionized water (2×~100 mL). The organic layer was separated, dried over anhydrous MgSO4 and the filtrate was removed in vacuo. The residue obtained was purified by crystallization from ethyl acetate and hexane to provide the hydrazide as a white solid (5.2 g, 76%).

H) 5-[4-(4-cyano-1-butyn-1-yl)phenyl]-1-(2,4-di-chlorophenyl)-N-(1,1-dioxido-4-thiomorpholinyl)-4-methyl-1H-pyrazole-3-carboxamide To a solution of the hydrazide (5 g, 11.4 mmol) in iPrOH (6 mL) was added divinyl sulfone (1.35 g, 11.4 mmol) dropwise and the contents were stirred overnight at room temperature. The white solids obtained were filtered and washed with iPrOH (2×25 ml) and re-dissolved in hot ethyl acetate to provide crystals when kept on standing overnight (3.5 g, 55%).

1H NMR (Varian Unity-INOVA spectrometer, 500 MHz, CDCl3): 8.08 (s, 1H), 7.43 (s, 1H), 7.37 (d, J=7.81 Hz, 2H), 7.28-7.34 (m, 1H), 7.24 (s, 1H), 7.06 (d, J=7.81 Hz, 2H), 3.56 (d, J=4.88 Hz, 4H), 3.26 (br. s., 4H), 2.72-2.87 (m, 2H), 2.57-2.71 (m, 2H), 2.37 (s, 3H); 13C NMR (125 MHz, CDCl3): 161.21, 144.23, 143.94, 136.69, 136.25, 133.36, 132.44, 130.97, 130.90, 129.92, 128.74, 128.49, 123.90, 118.92, 118.69, 87.43, 82.95, 53.50, 51.62, 18.12, 17.24, 9.85; HRMS-ESI (Q-TOF) calcd for C26H23Cl2N5O3S (M++H), 556.0977, found 556.0980. Elemental analysis Anal. Calcd for C26H23Cl2N5O3S: C % 56.12, H % 4.17, N % 12.59, S % 5.76; found C % 56.2, H % 4.04, N % 12.37, S % 5.59; m.p 278-280° C.; Heavy metals, USP<231> Method II less than 20 ppm; Palladium content not detectable by ICP-MS; Copper content 0.86 ppm by ICP-MS; Iron content 6.4 ppm by ICP-MS; Water content 0.3% (Karl Fisher).

Alternatively, the acid (15.8 mmol) obtained from step E scheme 1 was taken in a 500 ml 1 neck flask equipped with a nitrogen inlet and to it 200 ml of DCM, 4-aminothiomorpholine 1,1-dioxide (16.4 mmol), TBTU (17.4 mmol) and DIPEA (17.4 mmol) were added and the contents were stirred for 1 hour (scheme 4). To the reaction mixture, 100 ml of water was added, and the contents were acidified pH~7 using 2N HCl. The organic layer was separated, washed with brine, dried over sodium sulphate and concentrated to provide 5-[4-(4-cyano-1-butyn-1-yl)phenyl]-1-(2,4-dichlorophenyl)-N-(1,1-dioxido-4-thiomorpholinyl)-4-methyl-1H-pyrazole-3-carboxamide in 74% yields.

Example 2

A) 1-(2,4-dichlorophenyl)-4-methyl-3-(piperidin-1-ylcarbamoyl)-1H-pyrazol-5-yl trifluoromethanesulfonate To magnetically stirred suspension of AlCl3 (9.8 g, 3 eq) in anhydrous dichloroethane (30 ml) at 0° C. was added 1-aminopiperidine (8.6 g, 3.5 eq) under argon atmosphere, and the resulting mixture was stirred at 0-5° C. for 25 min. Ethyl 1-(2,4-dichlorophenyl)-4-methyl-5-(((trifluoromethyl)sulfonyl)oxy)-1H-pyrazole-3-carboxylate (11 g) in dichloroethane (250 ml) was added, and the reaction mixture was slowly brought to room temperature over 30 minutes, and stirred at this temperature for 5 h. Reaction was quenched by adding 10% HCl (50 ml), and the biphasic mixture was stirred for 2 h. Organic layer was separate, and the aqueous layer was extracted with dichloromethane (3×50 ml). Combined organic layers were washed with water (2×80 ml), and brine (1×80 ml), dried over anhydrous MgSO4, filtered and the solvent was removed in vacuo. The residue was purified by flash column chromatography on silica gel to give 9.5 g (77% yield) of product as a white solid.

B) 5-(4-chlorophenyl)-1-(2,4-dichlorophenyl)-4-methyl-N-(piperidin-1-yl)-1H-pyrazole-3-carboxamide 9 g of the pyrazole triflate of the preceding step, 2.8 g of 4-chlorophenylboronic acid and 350 mg of tetrakis(triphenylphosphine)palladium are mixed, under nitrogen; 250 ml of ethyl acetate and 35 ml of a 2M aqueous sodium carbonate solution are added. The reaction medium is stirred at 65° C. for 6 hours. The reaction medium is separated by settling out, the aqueous phase is discarded, and the organic phase is then washed with 100 ml of water. After separation by settling out, the organic phase is evaporated off. The crude product obtained is purified by filtration and crystallization from a mixture of ethyl acetate and hexane to provide the final product (6 g).

Example 3 (Schemes 3A and 3B)

A) Benzyl thiomorpholine-4-carboxylate-d8

To a solution of thiomorpholine-2,2,3,3,5,5,6,6-d8 (2 g) prepared as in WO2008070619, taken in 1N NaOH (11.6 mL) was added benzyl chloroformate (1.66 mL) under ice water cooling and the mixture was stirred at ambient temperature for 2 hours. The solution was neutralized with 1N HCl and extracted with EtOAc twice. The combined organic layer was washed with water and brine, dried over MgSO4 and evaporated in vacuo. The residue was purified by silica gel column chromatography to give benzyl thiomorpholine-4-carboxylate-d8 as a colorless Solid (4.8 g).

B) Benzyl thiomorpholine-4-carboxylate-2,2,3,3,5,5,6,6-d8 1,1-dioxide

To a solution of benzyl thiomorpholine-4-carboxylate-d8 (4.8 g) in methanol (30 mL) and H2O (20 mL) was added oxone (16.2 g) under ice water cooling and the mixture was stirred at ambient temperature for 2 hours. The solution was evaporated in vacuo and partitioned between EtOAc and water. The aqueous layer was extracted with EtOAc. The combined organic layer was washed with water and brine, dried over MgSO4 and evaporated in vacuo. The residue was purified by silica gel column chromatography eluting with a mixture of hexane and EtOAc to give the title compound (3.8 g).

C) Thiomorpholine 1,1-dioxide-d9

To a solution of benzyl thiomorpholine-4-carboxylate-2,2,3,3,5,5,6,6-d8 1,1-dioxide
(3.8 g) in methanol (32 mL) and 1,4-dioxane (8 mL) was added Palladium, 10 wt. % on activated carbon (380 mg) at ambient temperature. The mixture was stirred at ambient temperature for 4 hours under an environment of D2. The mixture was filtered and evaporated in vacuo to give title compound (2.22 g).

D) tert-Butyl (1,1-dioxidothiomorpholino-2,2,3,3,5,5,6,6-d8)carbamate

To a solution of thiomorpholine 1,1-dioxide-d9 (2 g) in CHCl3 (20 mL) was treated at 0 deg C. by a solution of tert-butyl 3-(4-cyanophenyl)-1,2-oxaziridine-2-carboxylate (3.4 g) in CHCl3 (20 mL). At the end of the addition the cooling bath was removed, and the contents were allowed to stir overnight. The solvent was evaporated, and the residue obtained was carried to the next step directly.

E) 4-Aminothiomorpholine 1,1-dioxide-2,2,3,3,5,5,6,6-d8

To a stirred solution of crude tert-butyl (1,1-dioxidothiomorpholino-2,2,3,3,5,5,6,6-d8)carbamate obtained in step D in dichloromethane (25 ml) at 0° C. was added trifluoroacetic acid (15 ml). After stirred at room temperature for 1 hour, the mixture was evaporated to give an oil. Diethyl ether (100 ml) was added, and the white precipitate was separated. The upper solution was then removed by decanting. This procedure was repeated three times to ensure complete removal of excess trifluoroacetic acid. The remaining white solids were dried in vacuo to give the title compound in quantitative yield.

F) 5-(4-(4-Cyanobut-1-yn-1-yl)phenyl)-1-(2,4-dichlorophenyl)-N-(1,1-dioxidothiomorpholino-2,2,3,3,5,5,6,6-d8)-4-methyl-1H-pyrazole-3-carboxamide The acid (7.5 g, 15.8 mmol) obtained from step E scheme 1 was taken in a 500 ml 1 neck flask equipped with a nitrogen inlet and to it 200 ml of DCM, 4-aminothiomorpholine 1,1-dioxide-2,2,3,3,5,5,6,6-d8 (2.61 g, 16.4 mmol), TBTU (5.59 g, 17.4 mmol) and DIPEA (2.25 g, 17.4 mmol) were added and the contents were stirred for 1 hour. To the reaction mixture, 100 ml of water was added, and the contents were acidified to pH ~7 using 2N HCl. The organic layer was separated, washed with brine, dried over sodium sulphate and concentrated to give the title compound (3 g); ES m/z 554.14 (M$^+$+H).

What is claimed is:
1. A process for preparing a compound represented by Formula IA, its solvates, polymorphs and isotopic variations thereof:

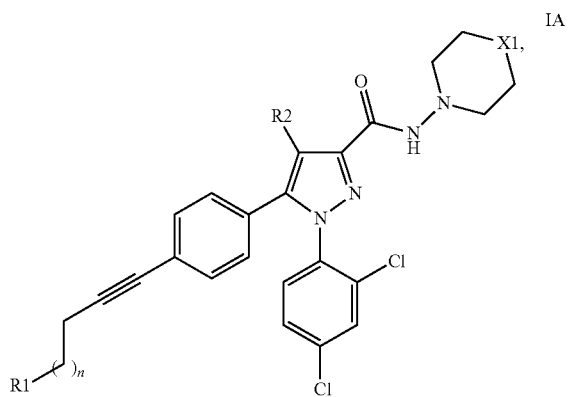

comprising:
reacting a compound represented by Formula II:

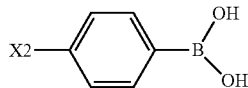

with a compound represented by Formula III:

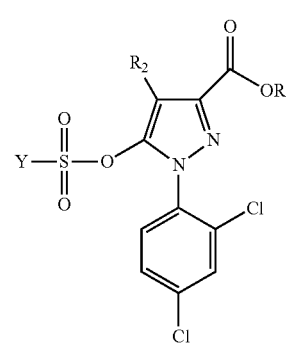

to provide a compound represented by Formula VII:

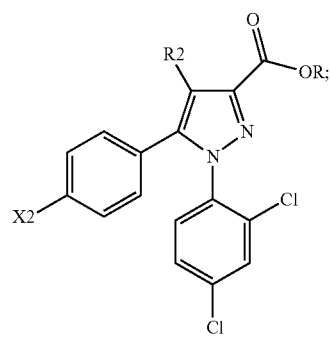

and
reacting the compound of Formula VII with an alkyne to provide a compound represented by formula I:

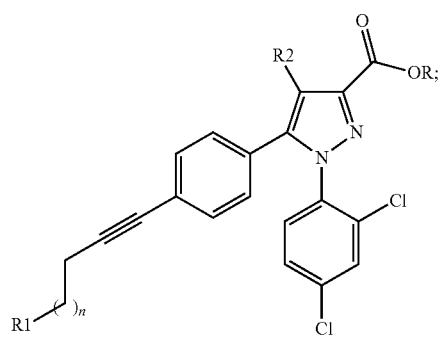

or
reacting a compound represented by Formula II:

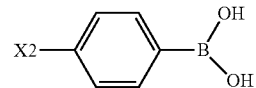

with a compound represented by Formula III:

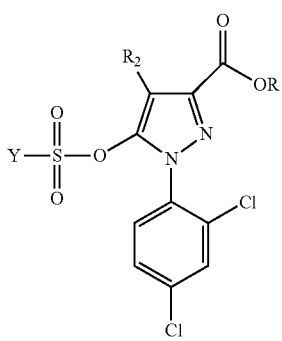

to provide a compound represented by Formula I:

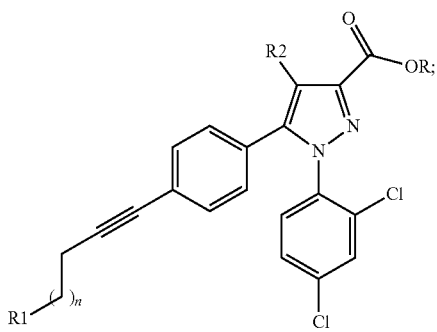

and
reacting the compound of Formula I with an alkali metal hydroxide to provide a compound represented by Formula V:

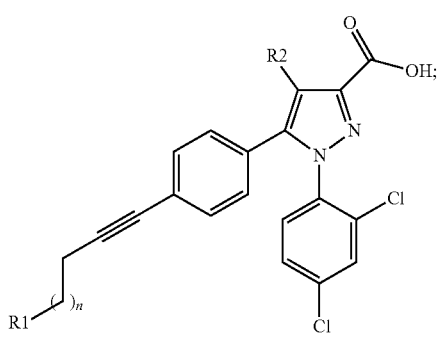

and
reacting the compound of Formula V with a substituted hydrazine to provide a compound represented by the Formula IA; or
reacting the compound of Formula I with a substituted hydrazine to provide a compound represented by Formula VI:

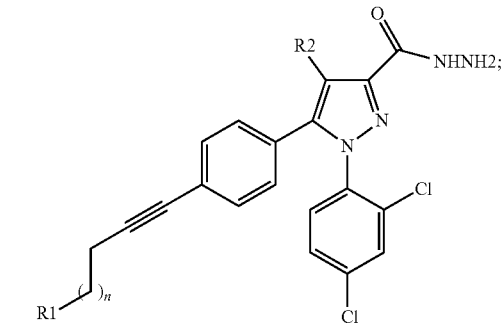

and
reacting the compound of Formula VI with a divinyl derivative to provide a compound represented by the Formula IA, wherein R is selected from the group consisting of H, $CH_3$ and $CH_2CH_3$;

R1 is selected from the group consisting of H, CN, OH, phthalimido, amide, carboxylic ester, nitrate ester, halogen, methoxy, mesylate and tosylate;

R2 is selected from the group consisting of H, $CH_3$, $CH_2CH_3$, $OCH_3$ and CN;

X1 is selected from the group consisting of $CH_2$, O and $SO_2$;

X2 is halogen or

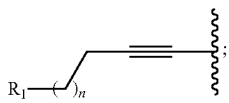

n is an integer from 1-4; and

Y is selected from the group consisting of a $C_1$-$C_4$ alkyl group, a $C_1$-$C_4$ perfluoroalkyl group, and a phenyl group that is unsubstituted or substituted with a methyl, chloro or nitro group.

2. The process of claim 1, comprising reacting a compound represent by Formula I:

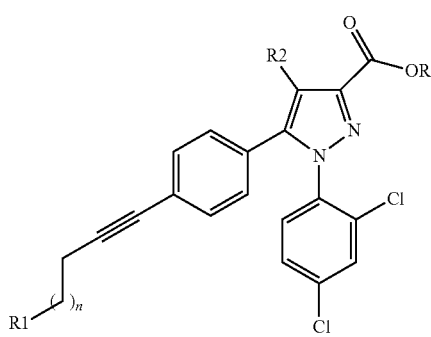

with a substituted hydrazine to provide a compound represented by Formula VI:

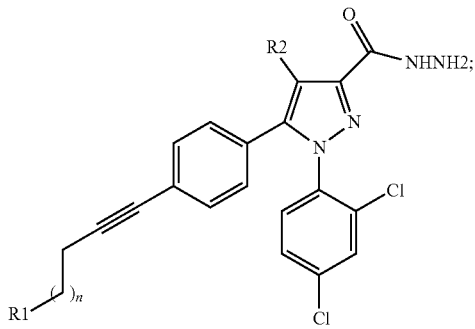

and
  reacting the compound of Formula VI with a divinyl derivative to provide a compound represented by the Formula IA, wherein
  R is CH₂CH₃.

3. The process of claim 1, comprising reacting a compound represented by Formula II:

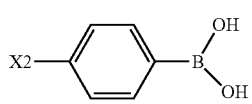

with a compound represented by Formula III:

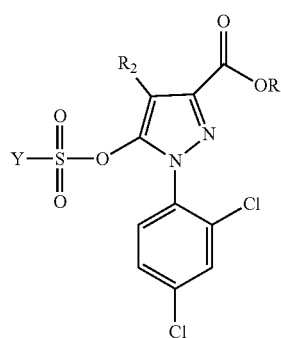

to provide a compound represented by Formula VII:

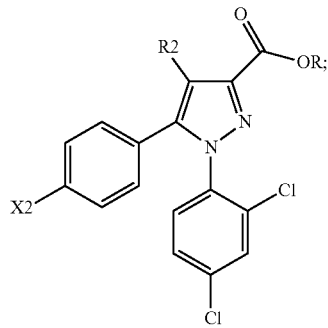

and
  reacting the compound of Formula VII with an alkyne to provide a compound represented by Formula I:

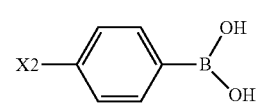

wherein
  R is selected from H, CH₃, CH₂CH₃; and
  X2 is Br.

4. The process of claim 3, comprising:
  reacting a compound represented by Formula II:

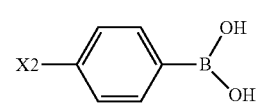

with a compound represented by Formula III:

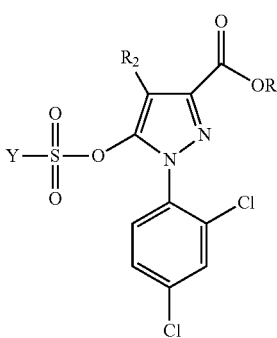

to provide a compound represented by Formula VII:

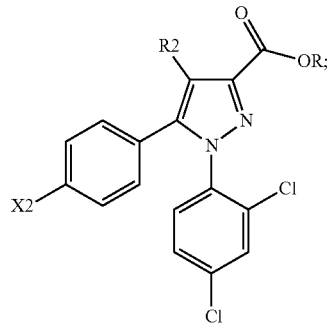

VII and reacting the compound of Formula VII with an alkyne to provide a compound represented by Formula I:

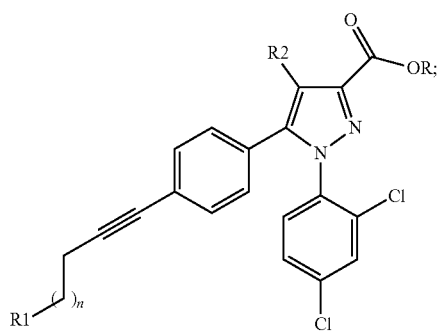

I wherein

R1 is OH or CN;

R2 is selected from the group consisting of $CH_3$, $CH_2CH_3$, $OCH_3$ and CN;

n is 1 or 2; and

Y is $CF_3$.

5. The process of claim 1, comprising:

reacting a compound represented by Formula II:

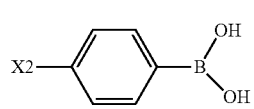

II with a compound represented by Formula III:

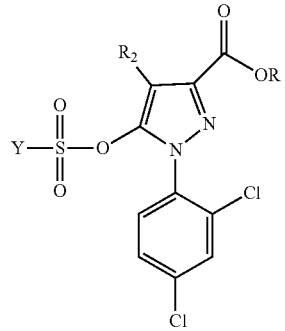

III to provide a compound represented by Formula I:

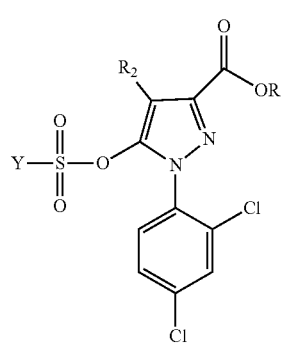

I

6. The process of claim 5, comprising:

reacting a compound represented by Formula II:

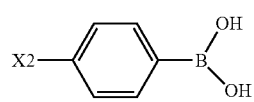

II with a compound represented by Formula III:

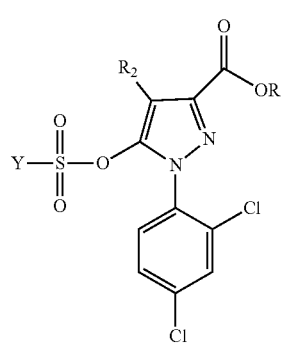

III to provide a compound represented by Formula I:

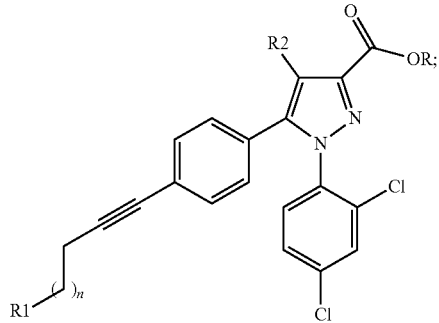

wherein
X2 is Br or

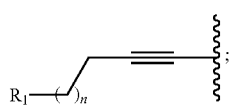

n is an integer from 1-4; and
Y is selected from the group consisting of a $C_1$-$C_4$ alkyl group, a $C_1$-$C_4$ perfluoroalkyl group, and a phenyl group that is unsubstituted or substituted with a methyl, chloro or nitro group.

7. A process for preparing a compound represented by Formula ID, its solvates, polymorphs and isotopic variations thereof

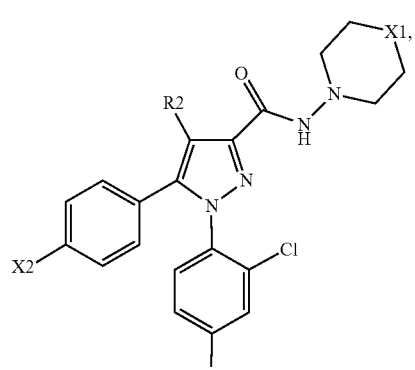

comprising:
reacting a compound represented by Formula III:

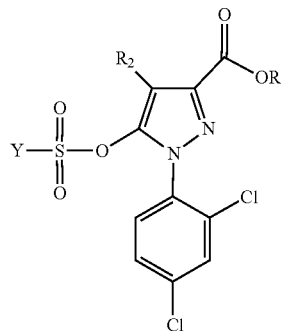

with substituted hydrazine to provide a compound represented by Formula IV:

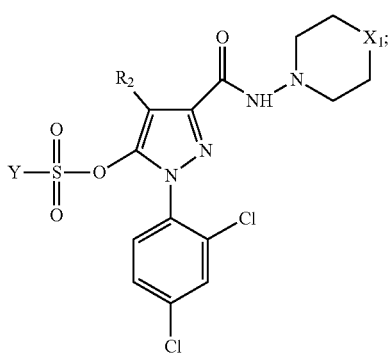

and
reacting the compound of Formula IV with a compound represented by Formula II:

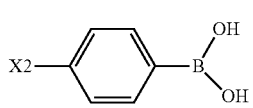

to provide a compound represented by the Formula ID, wherein
R is selected from H, $CH_3$, $CH_2CH_3$;
R1 is selected from the group consisting of H, CN, OH, phthalimido, amide, carboxylic ester, nitrate ester, halogen, methoxy, mesylate and tosylate;
R2 is selected from the group consisting of H, $CH_3$, $CH_2CH_3$, $OCH_3$ and CN;
X1 is selected from the group consisting of $CH_2$, O and $SO_2$;
X2 is Br or

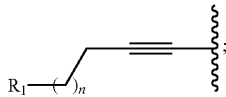

n is an integer from 1-4; and

Y is selected from the group consisting of a $C_1$-$C_4$ alkyl group, a $C_1$-$C_4$ perfluoroalkyl group, and a phenyl group that is unsubstituted or substituted with a methyl, chloro or nitro group.

8. The process of claim 1, wherein X1 is —SO$_2$—, —O— or —CH$_2$—.

9. The process of claim 7, wherein X1 is —SO$_2$—, —O— or —CH$_2$—.

10. The process of claim 1, comprising:
reacting a compound represented by Formula II:

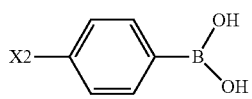

with a compound represented by Formula III:

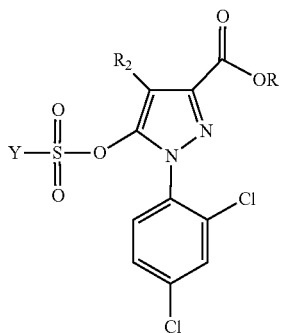

to provide a compound represented by Formula VII:

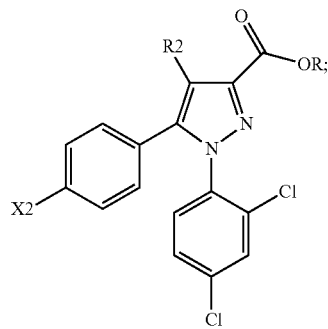

and
reacting the compound of Formula VII with an alkyne to provide a compound represented by formula I:

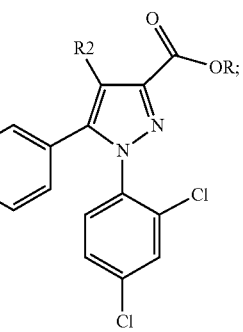

and
reacting the compound of Formula I with an alkali metal hydroxide to provide a compound represented by Formula V:

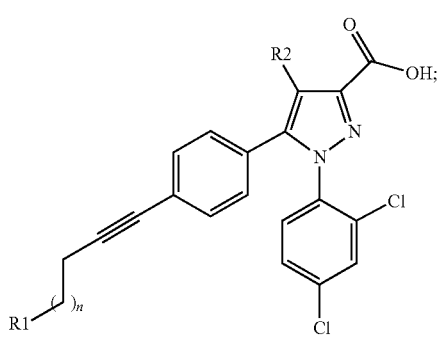

and
reacting the compound of Formula V with a substituted hydrazine; wherein
R is selected from CH$_3$ and CH$_2$CH$_3$;
R1 is selected from CN and OH;
R2 is selected from the group consisting of CH$_3$, CH$_2$CH$_3$, OCH$_3$ and CN;
X1 is selected from the group consisting of CH$_2$, O and SO$_2$;
n is an integer from 1-2;
X2 is Br; and
Y is CF$_3$.

11. The process of claim 1, comprising reacting a compound represented by Formula V:

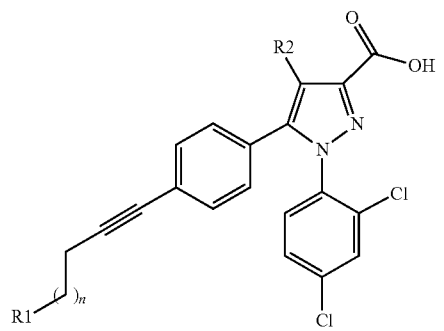

with a substituted hydrazine to provide a compound represented by one of Formulae IA, IB, IC, ID, and IG:
IA
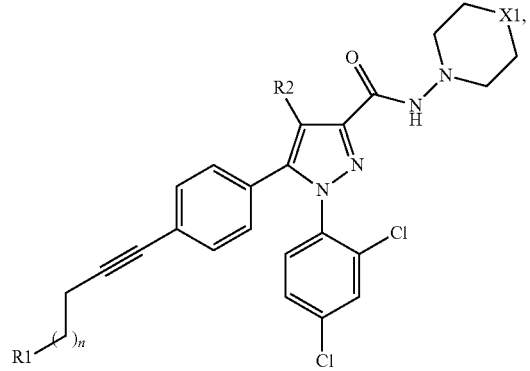
IB
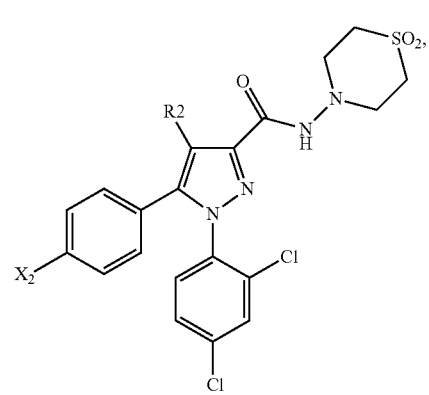
IC
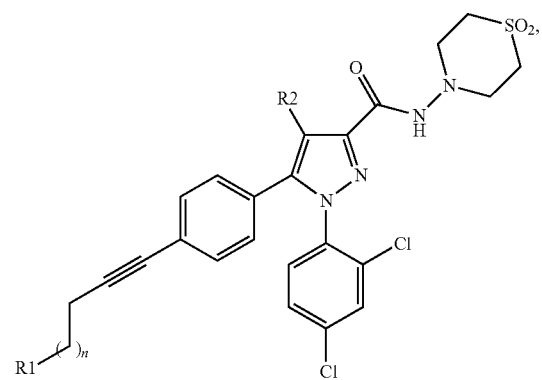
-continued
ID
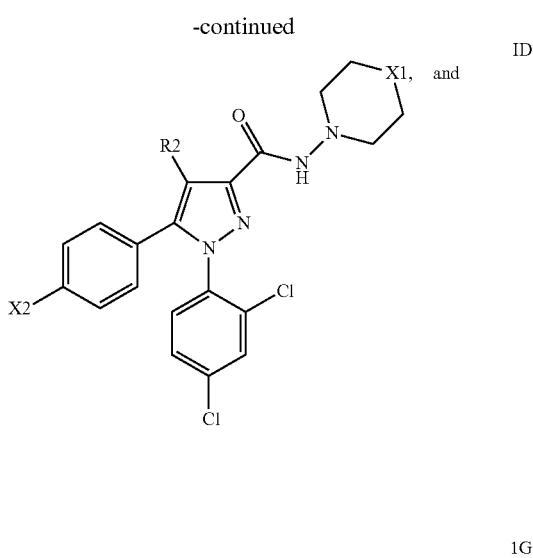 and
IG
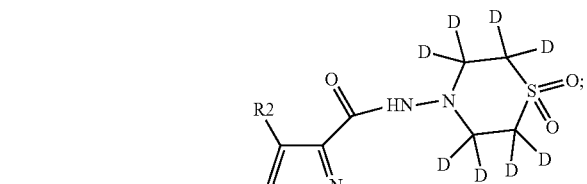
wherein
X2 is
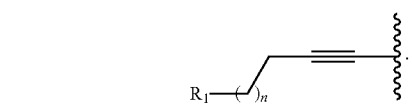
12. The process of claim 7, comprising reacting a compound represented by Formula VIII:
VIII
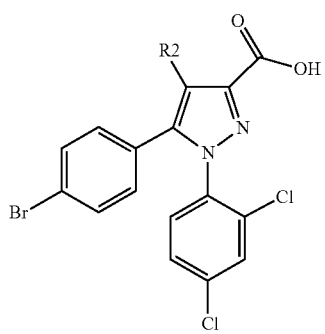

with a substituted hydrazine to provide a compound represented by one of Formulae IB, ID, IE and IF:
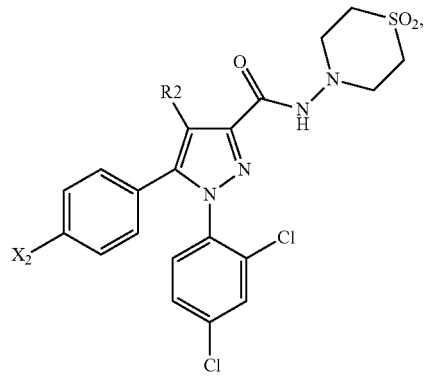
IB
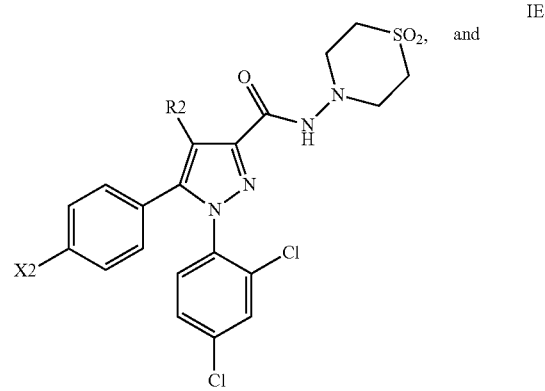
IE
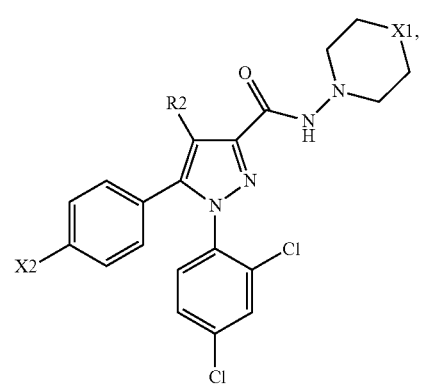
ID
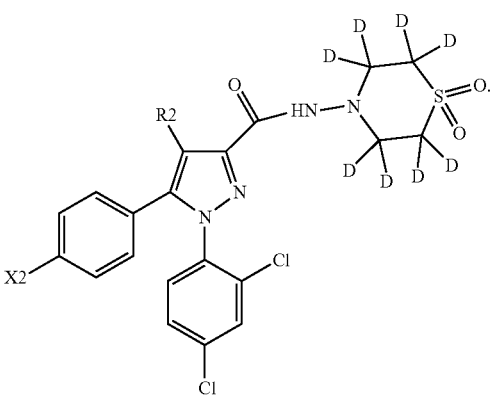
IF
and
* * * * *